United States Patent [19]

Masreliez

[11] 4,441,013
[45] Apr. 3, 1984

[54] DENTAL INSTRUMENT HEATER
[75] Inventor: Carl J. Masreliez, King County, Wash.
[73] Assignee: American Analytic Technology, Inc., Redmond, Wash.
[21] Appl. No.: 273,906
[22] Filed: Jun. 15, 1981
[51] Int. Cl.³ .............................................. H05B 1/00
[52] U.S. Cl. .................................. 219/231; 219/240; 219/242; 219/234; 320/40; 320/48; 320/2; 340/636; 433/32
[58] Field of Search ............... 219/234, 230, 231, 232, 219/242, 85 D, 240, 119; 320/2, 48, 39, 40; 340/636; 433/32

[56] References Cited
U.S. PATENT DOCUMENTS

| | | | |
|---|---|---|---|
| 1,092,307 | 4/1914 | Talbott | 219/230 |
| 2,140,817 | 12/1938 | Springall | 219/242 |
| 2,477,887 | 8/1949 | McMillan | 219/234 |
| 2,511,192 | 6/1950 | Barroso | 219/240 |
| 3,289,065 | 11/1966 | Dehmelt | 320/40 |
| 3,390,252 | 6/1968 | Storck | 219/119 |
| 3,553,561 | 1/1971 | Lesher | 320/39 |
| 3,560,704 | 2/1971 | Albert | 219/242 |
| 3,890,555 | 6/1975 | Nelson | 320/2 |
| 4,021,639 | 5/1977 | Espino | 219/242 |
| 4,354,092 | 10/1982 | Manabe | 320/2 |

Primary Examiner—B. A. Reynolds
Assistant Examiner—Teresa J. Walberg
Attorney, Agent, or Firm—Seed and Berry

[57] ABSTRACT

A dental instrument heater having a pair of contact blades connected to a battery. The contact blades have notches formed along their respective edges, and they are mounted in parallel, spaced-apart relationship to each other. Consequently, a dental instrument may be positioned between adjacent notches so that electric current from the battery flows through and heats the dental instrument. The heating device includes a self-contained charging circuit which connects an external charger to the battery when the battery voltage is below a predetermined value, and it disconnects the charger from the battery when the battery voltage reaches a predetermined level.

9 Claims, 5 Drawing Figures

DENTAL INSTRUMENT HEATER

DESCRIPTION

1. Technical Field

This invention relates to dental equipment, and more particularly, to an electronic device for heating conventional dental hand instruments.

2. Background Art

In the field of dentistry, it is often necessary to apply a heated instrument to the teeth of a patient for a variety of reasons, such as, for example, when sealing a root canal.

Conventional dental instruments, which are invariably of metal, are usually heated in conventional practice by inserting the tip of the instrument into an open frame generated by a device such as a Bunsen burner. Although this technique will, of course, provide the tip of the instrument with sufficient heat, it nevertheless entails a number of disadvantages. First, the use of a burner requires a fuel supply system and the need to maintain an adequate supply of fuel. For dental offices supplied with natural gas by utilities, maintaining an adequate supply is not a problem. However, it is not very cost effective to install natural gas conduits merely to be able to heat dental instruments. The use of other burner fuels require frequent refilling of the burner and the fuel may run out at an inopportune time.

Another problem with the use of conventional open-flame burners for heating dental instruments is the danger caused by the open flame. The burner is sometimes used around flammable gases or oxygen, which create a substantial fire hazard in the presence of the open flame. Also, of course, flammable objects, such as clothing, may inadvertently be ignited by the open flame.

Another disadvantage of open-flame burners used for heating dental instruments results from contamination of the instrument by the flame. Although the flame is sufficiently hot to kill germs, it often leaves deposits, such as carbon, on the surface of the instrument. This is undesirable for a number of reasons.

DISCLOSURE OF THE INVENTION

It is an object of the invention to heat a dental instrument without using an open flame.

It is another object of the invention to provide a dental instrument heater which is completely portable and which does not require the maintenance of a fuel supply.

It is still another object of the invention to provide a device for heating an instrument faster than when using a Busen burner.

It is a further object of the invention to provide an electric contact structure which facilitates good contact with the instrument.

It is a still further object of the invention to provide a battery charging circuit for a dental instrument heater which provides an indication of the charge status of the battery and which applies current to the battery only until full charge is reached.

These and other objects of the invention are provided by a dental instrument heater having a source of electrical power, such as a battery, and a pair of electrical contacts connected to the power source. The electrodes are preferably in the form of electrically conductive blades, each having a plurality of rectangular notches formed along adjacent edges when the blades are mounted in spaced-apart relationship to each other. The notches have a width larger than the transverse dimension of the dental instrument so that the dental instrument may be inserted between adjacent notches, thereby allowing current from the power source to flow through and heat the dental probe. As the dental instrument is forced against the side edge of one notch, it is also inherently forced against the opposite side edge of the adjacent blade in a lever action to assure good contact between the instrument and blades. The distance between the blades may be varied to adjust the magnitude, and hence, heating effect, of the current flowing through the dental instrument. Where a battery is used as the power source, the device includes a charging circuit which automatically disconnects the charging source from the battery when the battery is fully charged. Accordingly, the charging source is connected to the battery through a first switch which is opened by a circuit for measuring the voltage across the battery when the battery voltage reaches a predetermined level. The charging circuit includes indicator means responsive to the voltage measuring circuit for providing a visual indication of the charging condition of the battery.

BEST MODE FOR CARRYING OUT THE INVENTION

Figure 1:
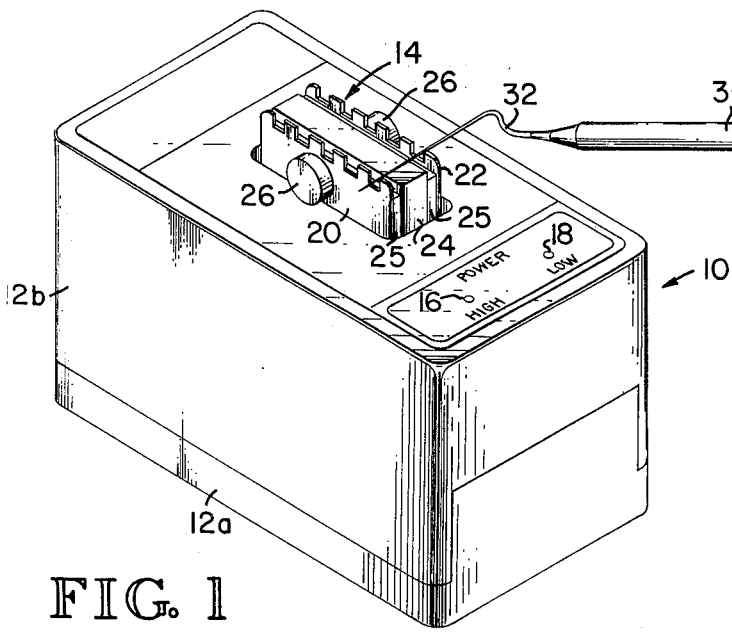
FIG. 1 is an isometric view of the dental instrument heater in use.
Figure 2:
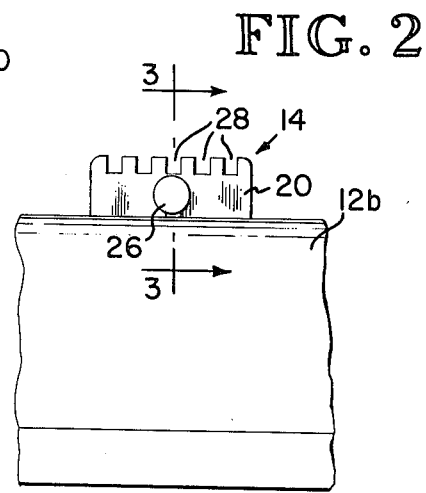
FIG. 2 is a side elevational view of a portion of the dental instrument heater.
Figure 3:
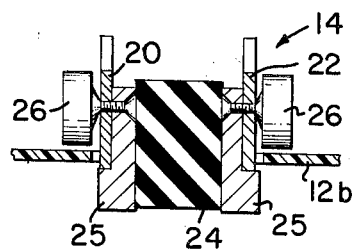
FIG. 3 is a cross-sectional view taken along the line 3—3 of FIG. 2.

The dental instrument heater 10, as illustrated in FIGS. 1–3, includes a housing 12 fabricated in two interfitting sections 12a,b. An electric contact assembly 14 projects upwardly from the upper surface of the housing 10, and a pair of indicator lamps 16,18 provide a visual indication of the condition of an internal battery.

The contact assembly 14 includes a pair of contact blades 20,22 positioned on opposite sides of an insulator block 24 and a pair of metal spacers 25, best illustrated in FIG. 3. The thickness of the spacers 25 or insulator block 24 may be varied to adjust the spacing between the blades 20,22, as desired, to control the current flow through the instrument. Alternatively, the thickness of the block 24 may progressively vary along its length so that the current flow through the instrument varies as it contacts different points along the blades 20,22. The blades 20,22 are held in contact with the spacers 25 by respective thumb screws 26.

As best illustrated in FIG. 2, a plurality of rectangularly shaped notches 28 are formed along the upper edge of each blade 20,22. In use, as illustrated in FIG. 1, a dental instrument 30 having a thin, electrically conductive tip 32 is positioned in adjacent notches 28 of the blades 20,22. As explained in greater detail hereinafter, the blades 20,22 are connected to opposite potentials of an electric power source so that current flows through the tip 32 from one blade 20 to other 22. It is important that the tip 32 contact opposite side edges of the notches 28 to achieve the best contact between the blades 20,22 and tip 32. Forcing the tip 32 against one side edge of a notch in blade 22 causes the tip 32 to pivot about that edge, thus forcing the tip 32 against the opposite side edge of the notch 28 of the other blade 20. If the tip 32 is forced against corresponding edges of the notches or the upper edges of the blades 20,22 (or if the upper edges of the blades were flat), the tip 32 would tend to pivot about that edge, thus moving the tip 32 away from the edge of the opposite blade 20. The notches 28, by allowing the tip 32 to exert equal and opposite forces on the adjacent notches, allow good contact between the tip 32 and blades 20,22 without a great deal of attention or care in positioning the probe.

Figure 4:
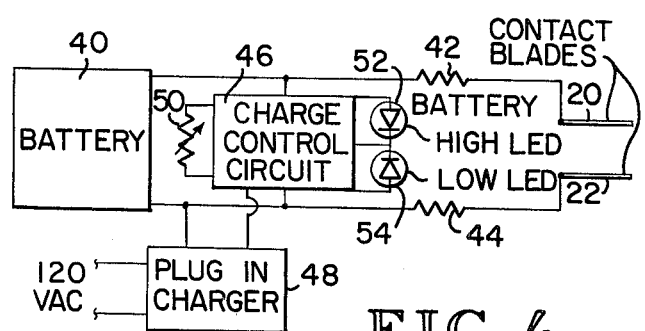
FIG. 4 is a block diagram of the dental instrument heater electronics.

A block diagram of the electronics for the dental instrument heater 10 is illustrated in FIG. 4. The device includes a battery 40 connected directly to the contact blades 20,22 through respective resistors 42,44. The resistors 42,44 limit the current flowing through the instrument when the instrument resistance is relatively low. However, they have relatively little effect on the current when the instrument resistance is relatively high. The resistors 42,44 thus regulate the current, and hence heating effect, to a relatively constant value despite substantial variations in the resistance of the instrument.

The battery 40 is also connected directly to a charge control circuit 46 which receives DC power from a conventional charger unit 48. The charger unit 48 receives 120-volt AC power from a conventional wall outlet. The charge control circuit 46 charges the battery 40 to a predetermined voltage as set by a resistor or potentiometer 50. The indicators 16, 18 are light-emitting diodes 52,54, respectively, connected to the charge control circuit 46. When battery 40 discharges to a predetermined voltage, the charge control circuit 46 causes current to flow through light-emitting diode 54, thereby indicating the need to recharge the battery. The plug-in charger 48, when connected to the charge control circuit 46, permits current to flow into the battery 40. When the battery 40 has been charged to a predetermined voltage, the charge control circuit 46 applies current through light-emitting diode 52, thereby indicating that the battery 40 is fully charged. The charge control circuit 46 then also disconnects the charger 48 from the battery 40 to prevent overcharging.

Figure 5:
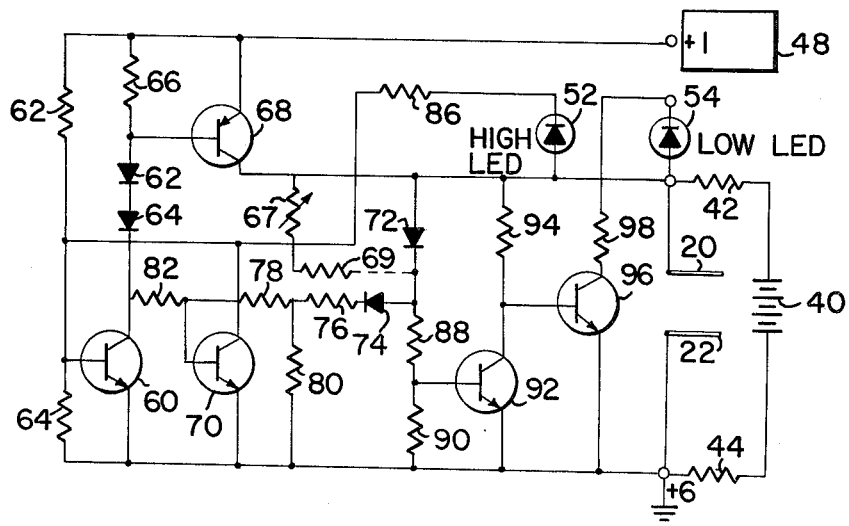
FIG. 5 is a schematic of the dental instrument heater electronics.

The charge control circuitry is illustrated in further detail in FIG. 5. In one operational embodiment, the battery 40 has a voltage of approximately 2.3 volts when fully charged. Accordingly, the charge control circuitry 46 is explained with reference to a 2.3-volt battery, but it will understood that it can be modified for any desired battery voltage. Assuming that the battery is somewhat discharged so that its voltage is significantly less than 2.3 volts, a DC voltage significantly greater than 2.3 volts is applied to the charge control circuit 46 by the charger 48. Transistor 60 is biased on since the voltage at its base, developed by voltage divider resistor 62,64, is greater than one diode drop. Current then flows through resistor 66 and diodes 62,64, creating a sufficient voltage drop across resistor 66 to saturate transistor 68. Transistor 68 thus connects the output of the charger 48 to the battery 40 through resistors 42,44.

After sufficient current has flowed into the battery, the voltage across the battery 40 approaches 2.3 volts. The voltage across the battery is applied to the base of transistor 70 through diodes 72,74 and resistors 76,78.

The base of transistor 70 is biased toward ground through resistor 80 when the diodes 72,74 are non-conducting. However, as the voltage across the battery 40 exceeds three diode drops (about 2.1 volts), the base-emitter junction of transistor 70 begins to conduct. As the voltage across the battery 40 continues to increase, the flow of current through transistor 70 also continues to increase. Finally, transistor 70 pulls sufficient current through resistor 62 to cause the base of transistor 60 to become back-biased, thereby terminating significant flow of current through resistor 66. This causes two functions to occur. First, the reduced voltage across resistor 66 cuts off transistor 68, thereby disconnecting the output of the charger 48 from the battery 40. Second, the increase in voltage at the collector of transistor 60 is applied to the base of transistor 70 through resistor 82. This increased voltage holds transistor 70 at saturation, even when the voltage across battery 40 decreases to some extent. It also causes transistors 60 and 70 to switch quickly as the transistor 70 begins to conduct.

The battery voltage at which transistors 60,70 switch may be made adjustable by utilizing a potentiometer 67 and resistor 69 instead of or in addition to the diode 72 with which they parallel. Reducing the resistance of the potentiometer causes the transistors 60,70 to switch at a lower battery voltage.

As mentioned above, as the battery 40 discharges, its voltage decreases. However, transistor 70 remains saturated because of the relatively high voltage on the collector of transistor 60 applied through resistor 82. It is not until the battery voltage falls significantly below 2.3 volts that the base of transistor 70 is pulled below the saturation point. However, when this occurs, the voltage drop across resistor 62 quickly increases to the point that transistor 60 becomes conductive, at which point the base of transistor 70 decreases to cut off transistor 70 and saturate transistor 60. Saturation of transistor 60 once again causes sufficient current to flow through resistor 66 to turn on transistor 68 and apply the output of the charger 48 to the battery 40. Transistors 60,70 thus operate in a hysteresis mode so that the battery voltage that the transistor 68 stops conducting is significantly greater than the battery voltage at which transistor 68 starts conducting.

The voltage across the battery 40 is also measured to provide a visual indication of the battery's condition. Accordingly, saturation of transistor 70 when transistor 68 cuts off, causes current to flow through light-emitting diode 52 and resistor 86, thereby illuminating the light-emitting diode 52 and providing a visual indication that the battery 40 has charged to its maximum voltage.

As long as the voltage across battery 40 is significantly larger than two diode drops (i.e., about 1.9 volts), sufficient voltage is developed across voltage divider resistors 88,90 to forward bias the base-emitter junction of transistor 92. Sufficient current thus flows through transistor 92 and resistor 94 to back-bias the base-emitter junction of transistor 96. However, as the voltage across the battery 40 approaches two diode drops, transistor 92 becomes less conductive. Eventually, the voltage drop across resistor 94 is sufficiently low to forward-bias the base-emitter junction of transistor 96, thus allowing current to flow from the battery through the light-emitting diode 54 and resistor 98. The light-emitting diode 54 thus provides a visual indication that the battery is in need of recharging.

Diodes 62,64 are provided to prevent current from flowing from the battery through the collector-base junction of transistor 68 to ground via transistor 60 in the event that the charger 48 is disconnected from the circuit. The diodes 62,64 provide an additional two semiconductor junctions in series with the collector-base junction of transistor 68. These three semiconductor junctions thus prevent current from flowing through the above-described discharge path when the battery voltage has decreased to 2.1 volts.

The dental instrument heater thus provides an efficient, relatively inexpensive, and easy-to-use device for heating a variety of dental instruments and similar devices. Further, use of the device is completely safe and convenient insofar as it requires no open flame or fuel supply.

I claim:

1. An electric heater for an electrically conductive dental instrument, comprising a source of electrical power and a pair of electrical contacts connected to said electrical power source, said electrical contacts including a pair of electrically conductive blades, each having a plurality of rectangular notches formed along one edge, said blades being mounted in transverse spaced-apart relationship with the notches of said blades being positioned adjacent each other, said notches having a width which is larger than the transverse dimension of said dental instrument and being free of any obstruction along a line extending transversely between and beyond adjacent notches so that said dental instrument may be inserted between adjacent notches while projecting transversely therefrom, thereby allowing current from said source to heat said dental instrument.

2. The dental instrument heater of claim 1 wherein the distance between said blades may be varied to adjust the magnitude of the current flowing through said dental instrument.

3. The dental instrument heater of claim 1 wherein said electrical power source is a battery and said heater further includes a charging circuit, comprising a DC power source, first switch means connected between said DC power source and said battery, detector means for measuring the voltage across said battery, and control means for opening said first switch means when said detector means determines that said battery is charged to a predetermined voltage.

4. The dental instrument heater of claim 3 wherein said charging circuit further includes means for providing a visual indication when said battery has charged to a predetermined voltage, comprising a light-emitting device and second switch means connected to said detector means for energizing light-emitting device when the voltage across said battery reaches a predetermined value.

5. The dental instrument heater of claim 4 wherein said charging circuit further includes means for providing a visual indication when said battery has discharged to a predetermined voltage, comprising a light-emitting device and second switch means connected to said detector means for energizing said light-emitting device when the voltage across said battery falls to said predetermined level.

6. The dental instrument heater of claim 3, further including means for providing a visual indication when said battery has discharged to a predetermined voltage, comprising a second light-emitting device and third switch means connected to said detector means for energizing said second light-emitting device when the voltage across said battery falls to said predetermined level.

7. The dental instrument heater of claim 3, further including means responsive to said detector means for closing said first switch means when said detector means determines that said battery has discharged to a voltage significantly lower than said predetermined voltage.

8. The dental instrument heater of claim 3, further including a resistor connected between said battery and one of said plates to regulate the current through said instrument to a relatively constant value as the resistance of said instrument varies.

9. The dental instrument of claim 1 wherein said electrically conductive blades are mounted on opposite sides of a lock of insulating material and secured thereto by respective thumbscrews, thereby facilitating the removal and replacement of said blades.

* * * * *